US012606855B2

(12) United States Patent
Yuan et al.

(10) Patent No.: US 12,606,855 B2
(45) Date of Patent: Apr. 21, 2026

(54) METHOD FOR SYNTHESIZING BETA-NICOTINAMIDE MONONUCLEOTIDE AND INTERMEDIATE THEREOF

(71) Applicant: Fujian Ribio Technology Co., Ltd., Sanming City (CN)

(72) Inventors: Yonghong Yuan, Tianjin (CN); Qi Pan, Tianjin (CN); Xiaoxue Guo, Tianjin (CN); Xusheng Zhao, Tianjin (CN)

(73) Assignee: Fujian Ribio Technology Co., Ltd., Sanming City (CN)

(*) Notice: Subject to any disclaimer, the term of this patent is extended or adjusted under 35 U.S.C. 154(b) by 728 days.

(21) Appl. No.: 18/011,455

(22) PCT Filed: Jun. 24, 2020

(86) PCT No.: PCT/CN2020/098277

§ 371 (c)(1),
(2) Date: Dec. 19, 2022

(87) PCT Pub. No.: WO2021/253476

PCT Pub. Date: Dec. 23, 2021

(65) Prior Publication Data

US 2023/0357811 A1 Nov. 9, 2023

(30) Foreign Application Priority Data

Jun. 19, 2020 (CN) ........................ 202010566477.1

(51) Int. Cl.
*C12P 19/30* (2006.01)
*C12N 9/16* (2006.01)

(52) U.S. Cl.
CPC ................ *C12P 19/30* (2013.01); *C12N 9/16* (2013.01); *C12Y 301/04003* (2013.01); *C12Y 301/04011* (2013.01)

(58) Field of Classification Search
CPC ... C12P 19/30; C12N 9/16; C12Y 301/04003; C12Y 301/04011
See application file for complete search history.

(56) References Cited

U.S. PATENT DOCUMENTS

2017/0121746 A1 5/2017 Velasquez et al.

FOREIGN PATENT DOCUMENTS

| | | | |
|---|---|---|---|
| CN | 106755209 | A | 5/2017 |
| CN | 107613990 | A | 1/2018 |
| CN | 108026130 | A | 5/2018 |
| CN | 108026535 | A | 5/2018 |
| CN | 108368493 | A | 8/2018 |
| CN | 108949865 | A | 12/2018 |
| CN | 109053838 | A | 12/2018 |
| CN | 110195089 | A | 9/2019 |
| CN | 110483601 | A | 11/2019 |
| CN | 111253448 | A | 6/2020 |
| WO | 2018023208 | A1 | 2/2018 |
| WO | 2018023210 | A1 | 2/2018 |

OTHER PUBLICATIONS

Lee et al. (ChemComm, 1999, 729) (Year: 1999).*
Yoshino et al. (Cell Metabolism, 2018, 27:513) (Year: 2018).*
Yoshino, Jun, et al. "Nicotinamide Mononucleotide, A Key NAD+ Intermediate, Treats the Pathophysiology of Diet-and Age-Induced Diabetes in Mice," Cell Metabolism, vol. 14, No. 4, pp. 528-536 (2011).
Mills, Kathryn F., et al. "Long-Term Administration of Nicotinamide Mononucleotide Mitigates Age-Associated Physiological Decline in Mice," Cell Metabolism, vol. 24, No. 6, pp. 795-806 (2016).
Lee, Jaemoon, et al., "A Chemical Synthesis of Nicotinamide Adenine Dinucleotide (NAD+)," Chemical Communications, pp. 729-730 (1999).
Zou, Yejun, et al. "Illuminating NAD+ Metabolism in Live Cells and In Vivo Using a Genetically Encoded Fluorescent Sensor," Developmental Cell, vol. 53, No. 2, pp. 240-252 (2020).
First Chinese Office Action corresponding to Application No. 202010566477.1, dated Jun. 17, 2021.

* cited by examiner

*Primary Examiner* — David Steadman
*Assistant Examiner* — Joseph R Spangler
(74) *Attorney, Agent, or Firm* — Hoffmann & Baron, LLP

(57) ABSTRACT

The present disclosure relates to a synthesis method of β-nicotinamide mononucleotide (β-NMN) and an intermediate thereof. In the present disclosure, phospholipid metabolism enzymes phospholipase D (PLD) and phospholipase C (PLC) widely present in the biosphere are used as catalysts to prepare β-NMN through two-step enzymolysis or one-pot synthesis; and an intermediate, namely phosphatidyl nicotinamide riboside (PNR), is obtained during the two-step enzymolysis. The present disclosure has simple reaction steps, low production cost, and environmental friendliness, and is suitable for large-scale industrial production.

16 Claims, 3 Drawing Sheets

Phospholipid

Phospholipid
NR
PNR
DAG
β-NMN

METHOD FOR SYNTHESIZING BETA-NICOTINAMIDE MONONUCLEOTIDE AND INTERMEDIATE THEREOF

CROSS-REFERENCE TO RELATED APPLICATION

This patent application is a U.S. national phase application of International Application No. PCT/CN2020/098277, filed Jun. 24, 2020, which claims the benefit and priority of Chinese Patent Application No. 202010566477.1, filed with the China National Intellectual Property Administration on Jun. 19, 2020, the disclosure of which is incorporated by reference herein in its entirety as part of the present application.

TECHNICAL FIELD

The present disclosure relates to a synthesis method of β-nicotinamide mononucleotide (β-NMN) and an intermediate thereof, and in particular relates to an enzymatic catalytic synthesis method of β-NMN and an intermediate phosphatidyl nicotinamide riboside (PNR) obtained during the synthesis of β-NMN.

BACKGROUND

β-NMN is a direct precursor for the synthesis of nicotinamide adenine dinucleotide ($NAD^+$, coenzyme I, a key cofactor in the metabolism of living organisms) and is present in almost all living organisms. β-NMN dominates hundreds of life activities in the human body and is an indispensable key factor in cellular energy metabolism, which catalyzes the production of 95% or more of the energy required for life activities. In order to maintain the normal functions of a living organism, a large amount of NMN needs to be synthesized in the living organism every day and then converted into coenzyme I. There is very little NMN in food, which is far from meeting the needs of the human body. For example, the vegetables edamame and broccoli with much NMN in the daily diet each have an NMN content of lower than 10 mg/kg on average, and an amount of NMN synthesized in the body of an adult every day is roughly equivalent to the intake of hundreds of kilograms of fruits and vegetables (Cell Metabolism, 2016, 24: 795-806).

Many studies have shown that an $NAD^+$ level often decreases with the aging of the human body, especially after middle age, an amount of coenzyme I ($NAD^+$) in the human body decreases sharply, which leads to various aging symptoms in the human body, such as memory loss, cardiovascular function attenuation, low immunity, poor resistance, decreased sleep quality, energy decline, constipation, hair loss, and appetite loss. In particular, in recent years, international authoritative academic journals have continued to publish human and animal studies, which repeatedly prove that the supplementation of NMN can effectively increase and restore a coenzyme I level in the body to greatly delay the aging and prevent the neuronal degenerative diseases such as Alzheimer's disease, thereby fundamentally regulating and improving various aging symptoms. Other studies have also involved cancer, infertility, obesity, cerebral hemorrhage, heart failure, heart damage, vascular aging, acute renal failure (ARF), diabetes, and the like, indicating that the supplementation of NMN has multifaceted medical and health care potential (Cell Metabolism, 2011, 14: 528-536; 2016, 24: 795-806). The exogenous supplementation of NMN, a precursor of $NAD^+$, can significantly increase an NAD level in bacteria and mammals, delay the progress of aging, and improve the vitality of life metabolism (Developmental Cell, 2020, 53: 240-252).

At present, there are many NMN health products on the market, and according to relevant statistics, users have reported diversified individual effects, including: energy improvement, physical strength improvement, fat loss and muscle gain, exercise capacity enhancement, skin improvement, hair loss reduction, hair growth promotion, sleep improvement, biological clock regulation, immune regulation, allergy reduction, sexual function enhancement, appetite boost, visual fatigue reduction, vision improvement, mood improvement, reduction in high blood sugar, reduction in high blood pressure, restoration of a low blood pressure to a normal level, constipation improvement, and the like.

The earliest attempts were made to produce NMN through a chemical method, where NR was often phosphorylated with phosphorus oxychloride to obtain the NMN (Chem. Commun. 1999, 729-730, CN 107613990 A). However, a product of the chemical method includes many impurities and is difficult to purify, and the chemical method has a low yield and a high comprehensive production cost, involves the use of a large number of toxic and harmful reagents to cause heavy pollution, and is not suitable for the production of food-grade NMN. Therefore, an enzymatic catalysis method to produce NMN has become the mainstream method for NMN production. There are many enzymatic catalytic synthesis methods for producing NMN, but most of these methods are related to NMN metabolism and synthesis in organisms, require the participation of various enzymes, and need to adopt expensive biomolecules such as adenosine triphosphate (ATP) as phosphate-based donors for NMN or adopt extremely expensive substrates.

For example, in the patents CN 108026130 A and CN 110195089 A, nicotinamide, ATP, and ribose are used as raw materials to produce NMN through a multi-step catalytic reaction enabled by nicotinamide phosphoribosyltransferase, ribose-phosphate pyrophosphokinase, and ribokinase.

In the patent CN 108026535A, nicotinamide, ATP, and adenosine monophosphate (AMP) are used as raw materials to produce NMN through a multi-step catalytic reaction enabled by nicotinamide phosphoribosyltransferase, ribose-phosphate pyrophosphokinase, and AMP nucleosidase.

In the patent PCT/CN2016/092457, nicotinamide, ATP, and xylose are used as raw materials to produce NMN through a multi-step reaction enabled by nicotinamide phosphoribosyltransferase, ribose-phosphate pyrophosphokinase, ribose-5-phosphate isomerase, ribulose-3-phosphate isomerase, xylulokinase, and xylose isomerase.

In the patent PCT/CN2016/092459, nicotinamide, pyrophosphoric acid, and AMP are used as raw materials to produce NMN through the catalysis of nicotinamide phosphoribosyltransferase and adenine phosphoribosyltransferase (APRT).

In the patent PCT/CN016/092461, nicotinamide, pyrophosphoric acid, and inosinic acid are used as raw materials to produce NMN through the catalysis of nicotinamide phosphoribosyltransferase, hypoxanthine phosphoribosyltransferase (HPRT), and xanthine oxidase (XO).

In the patents CN 108368493 A and CN 108949865 A, D-ribose 5-phosphate, ATP, and nicotinamide are used as raw materials to achieve the synthesis of NMN with phosphoribosyl pyrophosphate (PRPP) synthetase and nicotinamide phosphoribosyltransferase.

In the patent CN 106755209 A, NR and ATP are used as substrates to produce NMN through the catalysis of nicotinamide ribokinase.

In addition to ATP and other expensive bioactive molecules as substrates, the above enzymatic synthesis methods of NMN require a variety of unconventional enzymes, and these enzymes are expensive and not easy to produce. There are no commercialized enzyme preparations so far, and these enzymes need to be specifically prepared by NMN production enterprises, which makes an enzymatic production process of NMN very complex and costly. In addition, there is also a method for producing NMN through the catalysis with a single enzyme. For example, nicotinamide and 5'-phosphoribosyl-1'-pyrophosphate (PRPP) are used as substrates to produce NMN through the catalysis of nicotinamide phosphoribosyltransferase, but PRPP is expensive and is not easy to obtain. Thus, this method is not suitable for large-scale industrial production.

SUMMARY

In view of the many problems faced by the NMN production technologies mentioned in the above background, the present disclosure is intended to provide a brand-new enzymatic synthesis method for NMN. The brand-new enzymatic synthesis method is completely different from the natural biocatalytic synthesis system of NMN, does not at all involve the use of the above enzymes and expensive substrates such as ATP or PRPP, has simple reaction steps, low production cost, and environmental friendliness, and is suitable for large-scale industrial production.

In particular, the technical solutions of the present disclosure are as follows:

In order to achieve the above objective, through years of work accumulation and a large amount of experimental exploration, the inventors creatively invent an enzymatic synthesis route for NMN with NR as a substrate, a cheap phospholipid as a phosphorus-based donor, and phospholipase D (PLD) and phospholipase C (PLC) as catalysts (as shown in FIG. 1 and FIG. 2), which is a non-natural enzymatic catalytic synthesis route for NMN. The PLD and PLC are cheap and easy to obtain and have commercialized enzyme preparations. The entire reaction process of the synthesis route is simple, fast, and pollution-free, has a high product yield and a low production cost, and is suitable for large-scale industrial production.

A first objective of the present disclosure is to provide a two-step enzyme-catalyzed reaction (namely, sequential reactions) to produce NMN:

(a): two-step enzymolysis

- a1: with NR and a phospholipid as substrates, conducting a catalytic reaction under the catalysis of a PLD in the presence of a calcium ion to produce PNR; and
- a2: with the PNR produced in step a1 as a substrate, conducting a catalytic reaction under the catalysis of a PLC in the presence of a calcium ion to produce the β-NMN.

Further, with NR as a substrate and a phospholipid as a phosphatidyl donor, a reaction is allowed between the phospholipid and the NR under catalysis of PLD with a transphosphatidylation function to produce PNR, where PNR is a new phospholipid molecule that is easily separated from water-soluble NR; and subsequently, under the catalysis of PLC, PNR is hydrolyzed to produce diacylglycerol (DAG) and β-NMN, where DAG is a natural lipid that is insoluble in a reaction system and easily separated from water-soluble β-NMN.

A second objective of the present disclosure is to provide two routes for producing β-NMN through one-pot synthesis, specifically including:

- route 1: with NR and a phospholipid as substrates, in the presence of a calcium ion, adding a PLD to allow a reaction, and after the reaction is completed, adding a PLC to allow a reaction to obtain the β-NMN; and
- route 2: with NR and a phospholipid as substrates, in the presence of a calcium ion, adding a PLD and a PLC together to allow a reaction to obtain the β-NMN.

The phospholipid is a natural phospholipid or a synthetic phospholipid; further preferably, a main component of the phospholipid is phosphatidylcholine and/or phosphatidylethanolamine; and further preferably, the phospholipid is lecithin.

The phospholipid used in the present disclosure is preferably a natural phospholipid, which can be derived from a plant source such as *Glycine max* L., *Helianthus annuus* L., rapeseeds, and safflower seeds, an animal source such as cow's milk, goat's milk, deep-sea fish, deep-sea shrimps, and deep-sea scallops, or a microorganism source.

The phospholipid refers to a large class of compounds with similar phosphatidyl skeletons, and a structure thereof is shown in FIG. 1. The $R_1$ and $R_2$ parts in the phospholipid molecule are fatty acids, which can be any fatty acids such as short-chain, medium-chain, or long-chain fatty acids (LCFAs) and saturated fatty acids, monounsaturated fatty acids (MUFAs), or polyunsaturated fatty acids (PUFAs); $R_1$ and $R_2$ can be the same or different; and the rest will not be repeated here. The X part in the phospholipid molecule is a polar head, which is a hydroxyl-containing molecule and also has diversity; and common polar heads include choline, ethanolamine, inositol, glycerol, short-chain alcohol, or the like.

The PLC includes a broad-spectrum PLC and a phosphatidylinositol-specific phospholipase C (PIPLC); and further preferably, the PLC is a PIPLC.

The PLD is a PLD derived from an animal, a plant, or a microorganism; and further preferably, the PLD is a PLD derived from a microorganism, such as a PLD derived from *Streptomyces* spp.

According to the international system of enzyme nomenclature, the enzymes used in the above method include PLD and PLC. The PLD can catalyze a transphosphatidylation reaction, for example, the PLD can catalyze a reaction of phosphatidylcholine, phosphatidylethanolamine, or the like with a hydroxyl-containing substance to produce a corresponding phosphatidylation product, and a bond position of the phospholipid catalyzed thereby is shown in FIG. 1. The PLD can act on the P—O bond or O—X bond as shown in the figure, including, but not limited to, EC 3.1.4.4. There are many types of PLC, including, but not limited to, EC 3.1.4.3, EC 3.1.4.10, EC 3.1.4.11, and EC 4.6.1.13. The PLD can hydrolyze a glycerolphosphate bond of a phospholipid compound to produce DAG and a corresponding phosphate compound, and a bond position of the phospholipid catalyzed thereby is shown in FIG. 1.

The PLD and PLC used in the above method can be derived from an animal, a plant, or a microorganism, and PLD and PLC that each are derived from a microorganism or expressed by a microorganism are preferred. Specific forms of the PLD and PLC include enzyme solutions, enzyme lyophilized powders, enzyme-containing cells, and various immobilized enzymes and immobilized enzyme-containing cells, and the PLD and PLC may be unpurified crude enzymes, partially-purified or fully-purified enzymes, or commercial enzymes or may be specially produced. There are many types of PLC, where the broad-spectrum PLC and PIPLC are preferred.

In a1, the substrates NR and phospholipid exist simultaneously and can be mixed in any ratio. Preferably, a molar ratio of the NR to the phospholipid is 1:10 to 10:1; further preferably, the molar ratio of the NR to the phospholipid is 1:5 to 5:1; and further more preferably, the molar ratio of the NR to the phospholipid is 1:2 to 3:1.

In a1, during the reaction, a calcium salt needs to be added, and usually a soluble calcium salt is added, such as calcium chloride. In a1, a concentration of the calcium ion in a reaction system is 0.01 g/L to 20 g/L, and further preferably, the concentration of the calcium ion in the reaction system is 0.5 g/L to 5 g/L.

In a1, the catalytic reaction of the PLD is conducted at a temperature of 20° C. to 70° C. and a pH of 4.5 to 7.5; and further preferably, the catalytic reaction of the PLD is conducted at a temperature of 40° C. to 60° C. and a pH of 5.0 to 6.5.

During the catalytic reaction of the PLD in a1, an additive may be further added, and the additive includes, but is not limited to, one or more selected from the group consisting of n-hexane, n-heptane, and isopropanol.

Further preferably, based on a weight proportion, a content of the additive may be 0% to 50% when the additive is n-hexane or n-heptane and may be 0% to 30% when the additive is isopropanol.

During the catalytic reaction of the PLD, in order to adapt to the requirements of high-quality food production, the n-hexane, n-heptane, and/or isopropanol may not be added.

In a2, a concentration of the calcium ion in a reaction system is 0.01 g/L to 20 g/L, and further preferably, the concentration of the calcium ion in the reaction system is 0.1 g/L to 2 g/L.

In a2, the catalytic reaction of the PLC is conducted at a temperature of 20° C. to 70° C. and a pH of 4.0 to 7.0; and further preferably, the catalytic reaction of the PLC is conducted at a temperature of 40° C. to 55° C. and a pH of 5.0 to 7.0.

During the catalytic reaction of the PLC in a2, an alkane and/or a short-chain alcohol may be further added as an additive; the alkane may be one or two selected from the group consisting of n-hexane and n-heptane and the short-chain alcohol may be one or two selected from the group consisting of methanol, ethanol, propanol, isopropanol, butanol, and pentanol; and based on a weight proportion, a content of the alkane may be 0% to 80% and a content of the short-chain alcohol may be 0% to 30%.

During the catalytic reaction of the PLC, in order to adapt to the requirements of high-quality food production, the organic solvent additive may not be added.

In the two routes for preparing β-NMN through one-pot synthesis, the materials and technological means used in the preparation are basically the same as that in the two-step enzymolysis, which are not repeated here.

The PNR of the present disclosure has a structural formula as follows:

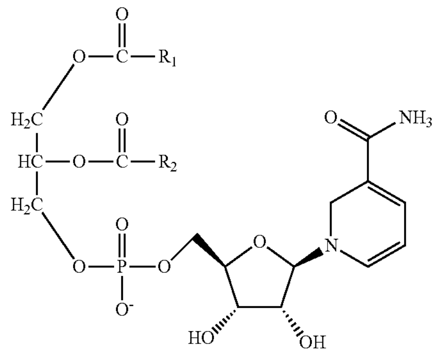

where $R_1$ and $R_2$ each are fatty acyl; natural phospholipids $R_1$ and $R_2$ are mostly LCFAs that are preferably selected from the group consisting of $C_{14-24}$ fatty acids and more preferably selected from the group consisting of $C_{16}$ and $C_{18}$ fatty acids; and further, $R_1$ is commonly $—C_{15}H_{31}$, $—C_{17}H_{35}$, or $—C_{17}H_{33}$ and $R_2$ is commonly $—C_{17}H_{31}$, $—C_{19}H_{29}$, $—C_{19}H_{31}$, $—C_{21}H_{31}$, or $—C_{17}H_{33}$.

Compared with the prior art, the present disclosure has the following advantages:

(1) In the present disclosure, a brand-new enzyme-catalyzed reaction route is provided to produce β-NMN, where with NR (a conventional β-NMN precursor) as a raw material and a phosphatidyl component in a phospholipid as a phosphatidyl donor, NR is subjected to phosphorylation through two-step enzyme catalysis to produce β-NMN.

(2) In the present disclosure, the phospholipid metabolism enzymes PLD and PLC widely present in the biosphere are used as catalysts, and their abilities to catalyze non-natural substrates are developed and utilized to produce β-NMN from a new intermediate PNR.

(3) The phospholipid (a phosphate-based donor) used in the present disclosure is a very cheap and common industrial raw material, and lecithin is the most well-known phospholipid. The enzymes used in the present disclosure are PLD and PLC, which are industrial enzyme preparations; and these enzymes are mostly used for the refining of vegetable oils such as soybean oil, are prone to heterogeneous expression, and have high activity and low price. The method of the present disclosure is suitable for large-scale industrial production.

DETAILED DESCRIPTION OF THE EMBODIMENTS

The substances mentioned above are tested.

1. Sampling and Analysis of NR and β-NMN During the Reaction.

In the reaction, the substrate NR and the product β-NMN are water-soluble compounds with strong polarity and need to be analyzed with a reversed-phase column.

A high-performance liquid chromatography (HPLC) analysis method for NR and β-NMN is as follows:

Chromatographic column: AGILENT SB-C18 (5 μm, 4.6×250 mm); and detection wavelength: 254 nm.

Mobile phases: mobile phase A and mobile phase B, which are combined according to Table 1 to conduct gradient elution with an initial flow rate of 0.8 mL/min and a column temperature of 30° C. Mobile phase A:water (1.36 g of monopotassium phosphate (MKP) is dissolved in 1 L of water, and a pH is adjusted with phosphoric acid to 2.5); and mobile phase B:methanol.

| Time/min | A % | B % |
|---|---|---|
| 0.01 | 95 | 5 |
| 5 | 95 | 5 |
| 11 | 5 | 95 |
| 15 | 5 | 95 |
| 16 | 95 | 5 |
| 25 | 95 | 5 |

2. Sampling and Analysis of the Phospholipid and PNR During the Reaction.

Figure 1:
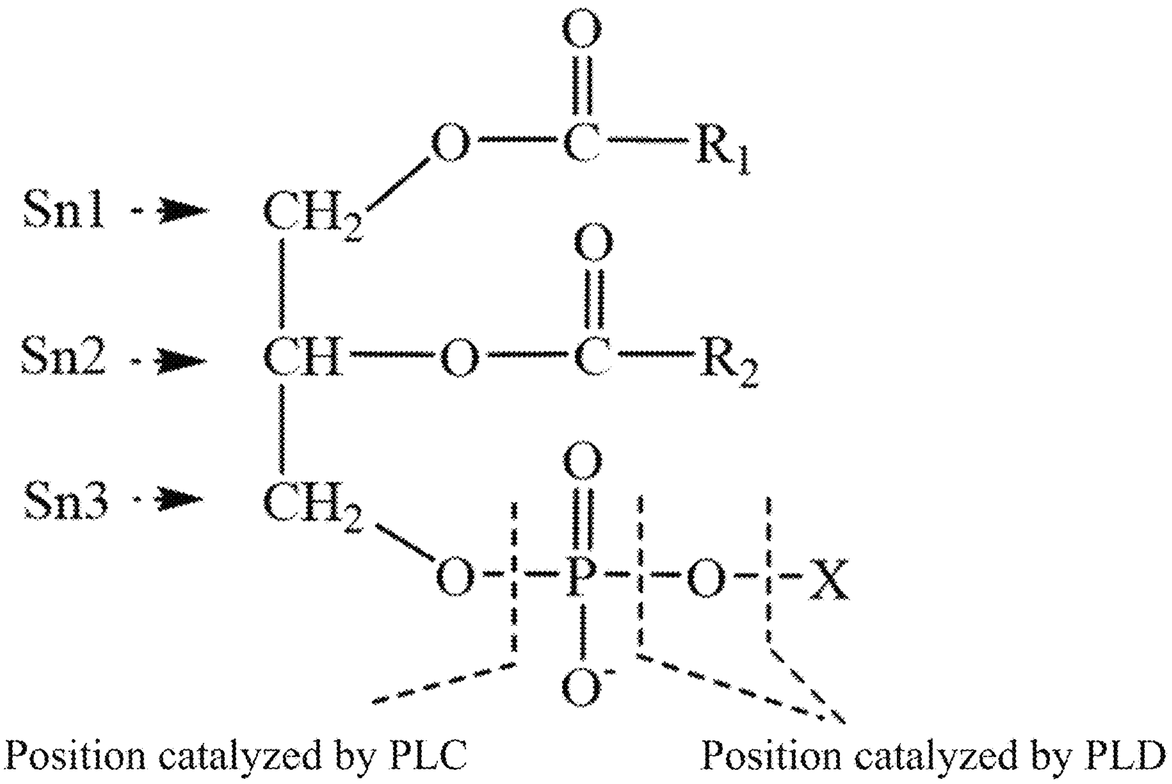
FIG. 1 shows action sites of the PLD and PLC of the present disclosure.
Figure 2:
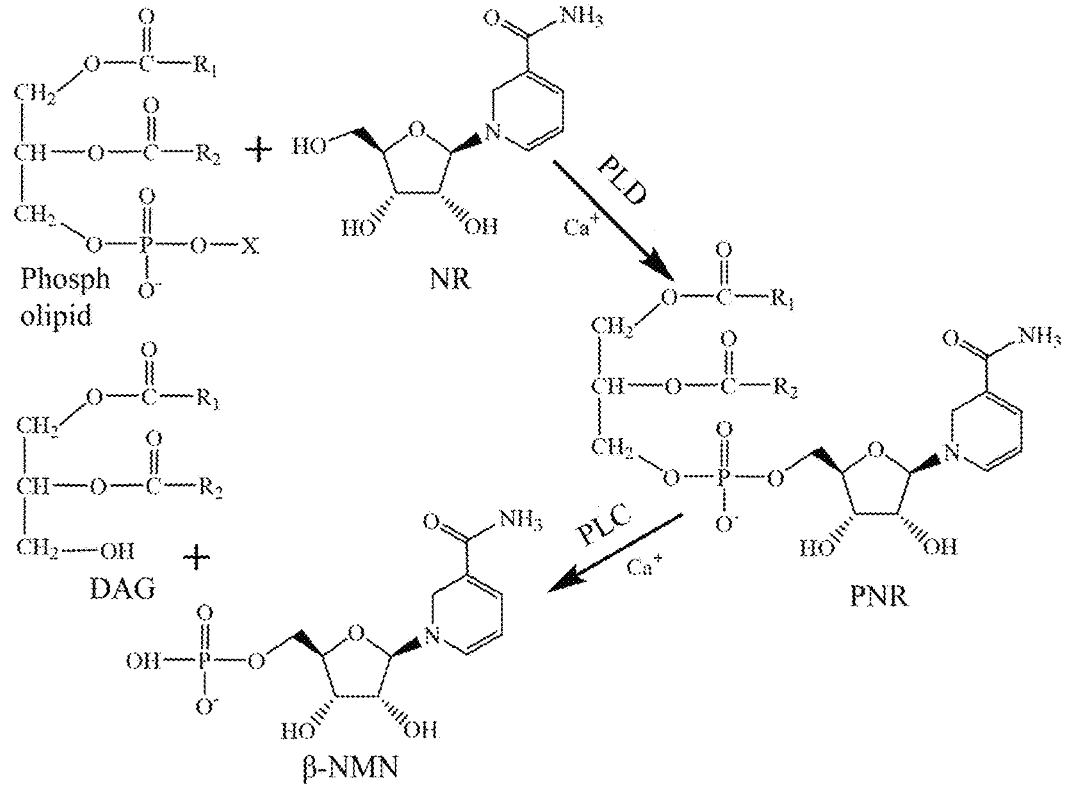
FIG. 2 is a schematic diagram illustrating the sequenced catalytic reactions of the PLD and PLC of the present disclosure.
Figure 3:
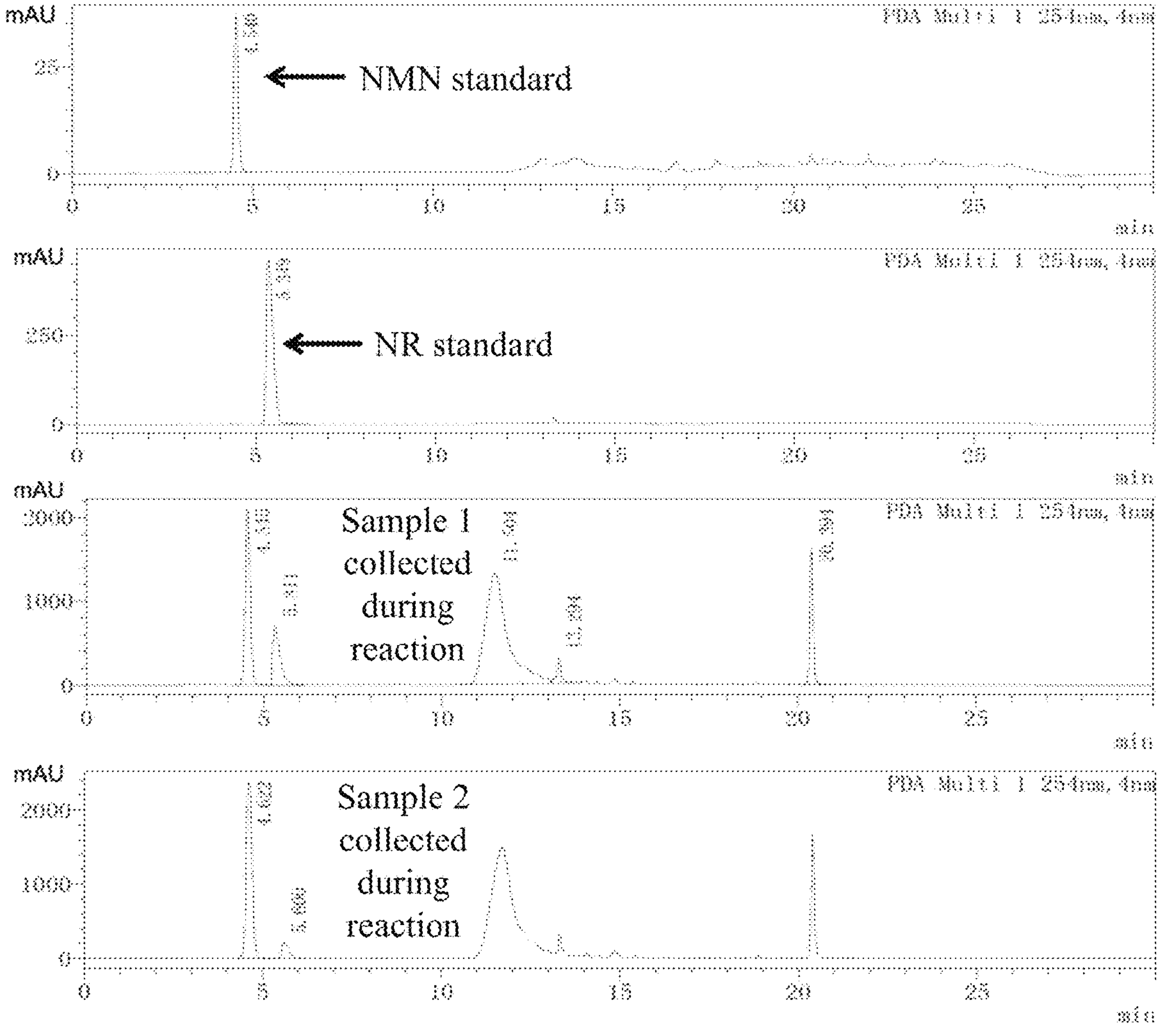
FIG. 3 shows liquid chromatography (LC) spectra for a reaction between NR and a phospholipid under the catalysis of the PLD of the present disclosure to produce PNR (before and after the reaction).
Figure 4:
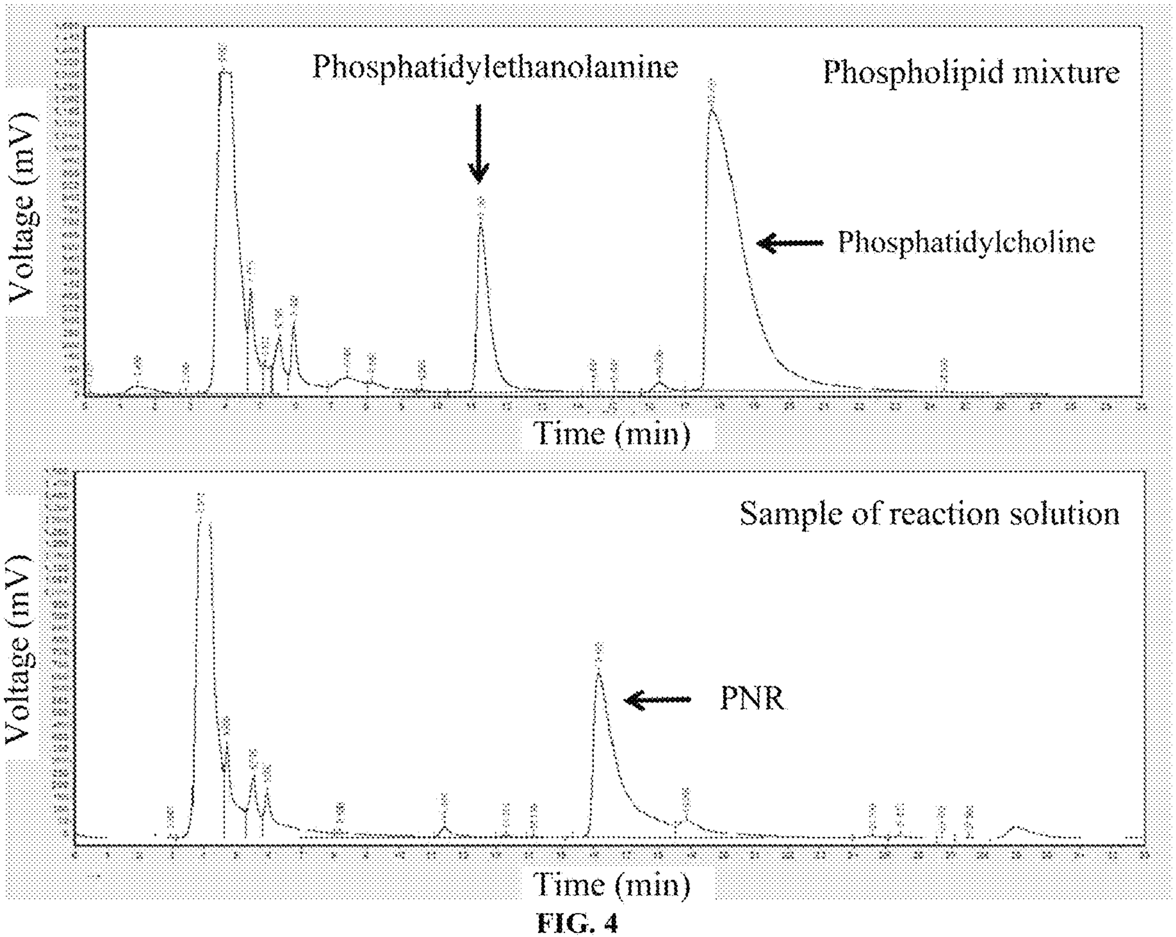
FIG. 4 shows LC spectra for the production of β-NMN under the catalysis of the PLC of the present disclosure from the PNR produced by the hydrolysis catalyzed by the PLD (standards of NR and NMN, and samples from an NMN reaction solution).

FIG. 4 shows the analysis of the substrate phospholipid and PNR in a sample taken during the reaction. During the reaction, the substrate phospholipid and the product PNR are water-insoluble compounds with weak polarity and need to be analyzed with a normal-phase column. An HPLC analysis method for the two is as follows: chromatographic column: silica gel column Si60 (5 μm, 4.5×250 mm); detection wavelength: 205 nm; analysis at room temperature; mobile phase: acetonitrile-methanol-85% phosphoric acid aqueous solution (100:10:1.8, V/V/V); isocratic constant-velocity analysis; and flow rate: 1.0 mL/min.

SPECIFIC EXAMPLES

Example 1

Preparation of PNR 1,000 L of a mixture of water, n-heptane, and isopropanol in a ratio of 5:4:1 was added to a reactor, then 150 g of a phospholipid (with 50% phosphatidylcholine-containing lecithin as an example) was added, and emulsification and dissolution were conducted; 50 kg of NR was added, and then 0.8 kg of calcium chloride was added; a resulting mixture was stirred and heated to 50° C. to 55° C. until the mixture was uniformly emulsified, and a pH was adjusted to 5.0 to 6.0 with a hydrochloric acid or sodium hydroxide solution; an appropriate amount of PLD was added to allow a reaction for about 2 h; and after the reaction was completed, a resulting reaction system was allowed to stand, and a resulting water-insoluble phase was separated to obtain 83 kg of PNR.

Example 2

Preparation of PNR 2,000 L of a mixture of water and isopropanol in a ratio of 8.5:1.5 was added to a reactor, then 500 g of a phospholipid (with 50% phosphatidylcholine-containing lecithin as an example) was added, and emulsification and dissolution were conducted; 120 kg of NR was added, and then 10 kg of calcium chloride was added; a resulting mixture was stirred and heated to 45° C. to 50° C. until the mixture was uniformly emulsified, and a pH was adjusted to 5.6 to 6.4 with a hydrochloric acid or sodium hydroxide solution; an appropriate amount of PLD was added to allow a reaction for about 1 h; and after the reaction was completed, a resulting reaction system was allowed to stand, and a resulting water-insoluble phase was separated to obtain 264 kg of PNR.

Example 3

Preparation of PNR 2,000 L of drinking water was added to a reactor, then 400 kg of a phospholipid (with 50% phosphatidylcholine-containing lecithin as an example) was added, and emulsification and dissolution were conducted; 140 kg of NR was added, and then 3 kg of calcium chloride was added; a resulting mixture was stirred and heated to 45° C. to 50° C. until the mixture was uniformly emulsified, and a pH was adjusted to 5.5 to 6.0 with a hydrochloric acid or sodium hydroxide solution; an appropriate amount of PLD was added to allow a reaction for about 4 h; and after the reaction was completed, a resulting reaction system was allowed to stand, and a resulting water-insoluble phase or water-insoluble substance was separated to obtain 218 kg of PNR.

Example 4

Preparation of PNR 2,000 L of a mixture of water, n-hexane, and isopropanol in a ratio of 6:3:1 was added to a reactor, then 240 g of a phospholipid (with 50% phosphatidylcholine-containing lecithin as an example) was added, and emulsification and dissolution were conducted; 20 kg of NR was added, and then 4 kg of calcium chloride was added; a resulting mixture was stirred and heated to 55° C. to 60° C. until the mixture was uniformly emulsified, and a pH was adjusted to 5.0 to 6.0 with a hydrochloric acid or sodium hydroxide solution; an appropriate amount of PLD was added to allow a reaction for about 1 h; and after the reaction was completed, a resulting reaction system was allowed to stand, and a resulting water-insoluble phase was separated to obtain 63 kg of PNR.

Example 5

Preparation of PNR 1,000 L of drinking water was added to a reactor, then 200 kg of a phospholipid (with 60% phosphatidylcholine-containing lecithin as an example) was added, and emulsification and dissolution were conducted; 150 kg of NR was added, and then 0.5 kg of calcium chloride was added; a resulting mixture was stirred and heated to 45° C. to 50° C. until the mixture was uniformly emulsified, and a pH was adjusted to 5.5 to 6.0 with a hydrochloric acid or sodium hydroxide solution; an appropriate amount of PLD was added to allow a reaction for about 4 h; and after the reaction was completed, a resulting reaction system was allowed to stand, and a resulting water-insoluble phase or water-insoluble substance was separated to obtain 115 kg of PNR.

Example 6

Preparation of PNR 3,000 L of a mixture of water, n-heptane, and isopropanol in a ratio of 7.5:2:0.5 was added to a reactor, then 500 kg of a phospholipid (with 30% phosphatidylcholine-containing lecithin as an example) was added, and emulsification and dissolution were conducted; 100 kg of NR was added, and then 20 kg of calcium chloride was added; a resulting mixture was stirred and heated to 47° C. to 52° C. until the mixture was uniformly emulsified, and a pH was adjusted to 5.5 to 6.0; an appropriate amount of PLD was added to allow a reaction for about 12 h; and after the reaction was completed, a resulting reaction system was allowed to stand, and a resulting water-insoluble phase was separated to obtain 163 kg of PNR.

Example 7

Synthesis Method of β-NMN 150 kg of the PNR from Examples 1 and 6 was taken, 100 kg of water, 10 kg of n-heptane, 5 kg of isopropanol, and 200 g of calcium chloride were added, a resulting mixture was thoroughly stirred and heated to 43° C. to 48° C., and a pH was adjusted to 5.5 to 6.0; and an appropriate amount of PLC was added to allow a reaction for about 2 h to obtain 52 kg of β-NMN.

Example 8

Synthesis Method of β-NMN 100 kg of PNR from Examples 3 and 5 was taken, 200 kg of drinking water and 0.5 kg of calcium chloride were added, a resulting mixture was thoroughly stirred and heated to 45° C. to 50° C., and a pH was adjusted to 6.0 to 6.5; and an appropriate amount of PLC was added to allow a reaction for about 4 h to obtain 34 kg of β-NMN.

Example 9

Synthesis Method of β-NMN 200 kg of PNR from Example 2 was taken, 880 kg of drinking water, 120 kg of isopropanol, and 2 kg of calcium chloride were added, a resulting mixture was thoroughly stirred and heated to 43° C. to 48° C., and a pH was adjusted to 6.0 to 6.5; and an appropriate amount of PLC was added to allow a reaction for about 8 h to obtain 70 kg of β-NMN.

Example 10

Synthesis Method of β-NMN 50 kg of the PNR from Example 4 was taken, 100 kg of water, 7 kg of n-hexane, 3 kg of isopropanol, and 80 g of calcium chloride were added, a resulting mixture was thoroughly stirred and heated to 45° C. to 50° C., and a pH was adjusted to 6.0 to 6.5; and an appropriate amount of PLC was added to allow a reaction for about 1 h to obtain 16 kg of β-NMN.

Example 11

Synthesis Method of β-NMN 100 kg of PNR from Examples 3 and 5 was taken, 300 kg of drinking water, 30 kg of butanol, and 2 kg of calcium chloride were added, a resulting mixture was thoroughly stirred and heated to 45° C. to 50° C., and a pH was adjusted to 6.5 to 7.0; and an appropriate amount of PLC was added to allow a reaction for about 2 h to obtain 34 kg of β-NMN.

Example 12

Synthesis Method of β-NMN 100 kg of PNR from Examples 3 and 5 was taken, 300 kg of drinking water, 30 kg of ethanol, and 2 kg of calcium chloride were added, a resulting mixture was thoroughly stirred and heated to 45° C. to 50° C., and a pH was adjusted to 6.5 to 7.0; and an appropriate amount of PLC was added to allow a reaction for about 2 h to obtain 33 kg of β-NMN.

Example 13

Preparation of β-NMN Through One-Pot Synthesis in which Enzymes were Added Successively 2,000 L of a mixture of water, n-heptane, and isopropanol in a ratio of 6:4:1 was added to a reactor, then 360 g of a phospholipid (with 50% phosphatidylcholine-containing lecithin as an example) was added, and emulsification and dissolution were conducted; 120 kg of NR was added, and then 2 kg of calcium chloride was added; a resulting mixture was stirred and heated to 47° C. to 52° C. until the mixture was homogeneous, and a pH was adjusted to 5.5 to 6.0; and an appropriate amount of PLD was added to allow a reaction for about 2 h; and then PLC was added, a temperature was adjusted to 43° C. to 48° C., and a reaction was conducted for about 4 h to obtain 71 kg of β-NMN.

Example 14

Preparation of β-NMN Through One-Pot Synthesis in Which Enzymes Were Added Successively 3,000 L of a mixture of water and isopropanol in a ratio of 8:2 was added to a reactor, then 450 g of a phospholipid (with 50% phosphatidylcholine-containing lecithin as an example) was added, and emulsification and dissolution were conducted; 90 kg of NR was added, and then 6 kg of calcium chloride was added; a resulting mixture was stirred and heated to 48° C. to 53° C. until the mixture was uniformly emulsified, and a pH was adjusted to 5.5 to 6.0; an appropriate amount of PLD was added to allow a reaction for about 2 h; and then PLC was added, a pH was adjusted to 6.0 to 6.5, and a reaction was conducted for about 4 h to obtain 92 kg of β-NMN.

Example 15

Preparation of β-NMN Through One-Pot Synthesis in Which Enzymes Were Added Successively 2,000 L of drinking water was added to a reactor, then 400 kg of a phospholipid (with 50% phosphatidylcholine-containing lecithin as an example) was added, and emulsification and dissolution were conducted; 90 kg of NR was added, and then 1.5 kg of calcium chloride was added; a resulting mixture was stirred and heated to 45° C. to 50° C. until the mixture was uniformly emulsified, and a pH was adjusted to 5.5 to 6.0 with a hydrochloric acid or sodium hydroxide solution; an appropriate amount of PLD was added to allow a reaction for about 3 h; and then PLC was added, a temperature was adjusted to 43° C. to 48° C. and a pH was adjusted to 6.0 to 6.5, and a reaction was conducted for about 6 h to obtain 83 kg of β-NMN.

Example 16

Preparation of β-NMN Through One-Pot Synthesis in Which Enzymes Were Added Successively 3,000 L of a mixture of water, n-hexane, and isopropanol in a ratio of 6:3:1 was added to a reactor, then 500 kg of a phospholipid (with 50% phosphatidylcholine-containing lecithin as an example) was added, and emulsification and dissolution were conducted; 120 kg of NR was added, and then 5 kg of calcium chloride was added; a resulting mixture was stirred and heated to 55° C. to 60° C. until the mixture was uniformly emulsified, and a pH was adjusted to 5.5 to 6.0 with a hydrochloric acid or sodium hydroxide solution; an appropriate amount of PLD was added to allow a reaction for about 2 h; and then PLC was added, a temperature was adjusted to 43° C. to 48° C. and a pH was adjusted to 6.0 to 6.5, and a reaction was conducted for about 3 h to obtain 99 kg of β-NMN.

Example 17

Preparation of β-NMN Through One-Pot Synthesis in Which Enzymes Were Added Successively 2,000 L of drinking water was added to a reactor, then 350 kg of a phospholipid (with 60% phosphatidylcholine-containing lecithin as an example) was added, and emulsification and dissolution were conducted; 120 kg of NR was added, and then 1 kg of calcium chloride was added; a resulting mixture was stirred and heated to 48° C. to 53° C. until the mixture was uniformly emulsified, and a pH was adjusted to 5.5 to 6.0 with a hydrochloric acid or sodium hydroxide solution; an appropriate amount of PLD was added to allow a reaction for about 4 h; and then PLC was added, a temperature was adjusted to 43° C. to 48° C. and a pH was adjusted to 6.0 to 6.5, and a reaction was conducted for about 1 h to obtain 86 kg of β-NMN.

Example 18

Preparation of β-NMN Through One-Pot Synthesis in Which Enzymes Were Added Successively 5,000 L of a mixture of water, n-heptane, and isopropanol in a ratio of 7.5:2:0.5 was added to a reactor, then 1,000 kg of a phospholipid (with 40% phosphatidylcholine-containing lecithin as an example) was added, and emulsification and dissolution were conducted; 150 kg of NR was added, and then 20 kg of calcium chloride was added; a resulting mixture was stirred and heated to 47° C. to 52° C. until the mixture was uniformly emulsified, and a pH was adjusted to 5.5 to 6.0; an appropriate amount of PLD was added to allow a reaction for about 6 h; and then PLC was added, a temperature was adjusted to 43° C. to 48° C. and a pH was adjusted to 6.0 to 6.5, and a reaction was conducted for about 6 h to obtain 157 kg of β-NMN.

Example 19

Preparation of β-NMN Through One-Pot Synthesis in Which Enzymes Were Added Simultaneously 3,000 L of a mixture of water and isopropanol in a ratio of 9:1 was added to a reactor, then 500 g of a phospholipid (with 50% phosphatidylcholine-containing lecithin as an example) was added, and emulsification and dissolution were conducted; 100 kg of NR was added, and then 3 kg of calcium chloride was added; a resulting mixture was stirred and heated to 45° C. to 50° C. until the mixture was uniformly emulsified, and a pH was adjusted to 5.8 to 6.3; and PLD and PLC were added simultaneously to allow a reaction for about 4 h to obtain 100 kg of β-NMN.

Example 20

Preparation of β-NMN Through One-Pot Synthesis in Which Enzymes Were Added Simultaneously 2,000 L of drinking water was added to a reactor, then 400 kg of a phospholipid (with 50% phosphatidylcholine-containing lecithin as an example) was added, and emulsification and dissolution were conducted; 80 kg of NR was added, and then 2 kg of calcium chloride was added; a resulting mixture was stirred and heated to 45° C. to 50° C. until the mixture was uniformly emulsified, and a pH was adjusted to 5.8 to 6.3 with a hydrochloric acid or sodium hydroxide solution; and PLD and PLC were added simultaneously to allow a reaction for about 5 h to obtain 82 kg of β-NMN.

Example 21

Preparation of β-NMN Through One-Pot Synthesis in Which Enzymes Were Added Simultaneously 2,000 L of drinking water was added to a reactor, then 300 kg of a phospholipid (with 60% phosphatidylcholine-containing lecithin as an example) was added, and emulsification and dissolution were conducted; 72 kg of NR was added, and then 1 kg of calcium chloride was added; a resulting mixture was stirred and heated to 45° C. to 50° C. until the mixture was uniformly emulsified, and a pH was adjusted to 5.8 to 6.3 with a hydrochloric acid or sodium hydroxide solution; and PLD and PLC were added simultaneously to allow a reaction for about 3 h to obtain 74 kg of β-NMN.

Example 22

Preparation of β-NMN Through One-Pot Synthesis in Which Enzymes Were Added Simultaneously 5,000 L of drinking water was added to a reactor, then 1,000 kg of a phospholipid (with 40% phosphatidylcholine-containing lecithin as an example) was added, and emulsification and dissolution were conducted; 175 kg of NR was added, and then 10 kg of calcium chloride was added; a resulting mixture was stirred and heated to 45° C. to 50° C. until the mixture was uniformly emulsified, and a pH was adjusted to 5.8 to 6.3 with a hydrochloric acid or sodium hydroxide solution; and PLD and PLC were added simultaneously to allow a reaction for about 8 h to obtain 167 kg of β-NMN.

Example 23

Preparation of β-NMN Through One-Pot Synthesis in Which Enzymes Were Added Simultaneously 3,000 L of a mixture of water, n-heptane, and isopropanol in a ratio of 6:3:1 was added to a reactor, then 750 kg of a phospholipid (with 50% phosphatidylcholine-containing lecithin as an example) was added, and emulsification and dissolution were conducted; 200 kg of NR was added, and then 7 kg of calcium chloride was added; a resulting mixture was heated to 45° C. to 50° C., and a pH was adjusted to 5.8 to 6.3 with a hydrochloric acid or sodium hydroxide solution; and PLD and PLC were added simultaneously to allow a reaction for about 12 h to obtain 128 kg of β-NMN.

Example 24

Preparation of β-NMN Through One-Pot Synthesis in Which Enzymes Were Added Simultaneously 3,000 L of drinking water was added to a reactor, then 550 kg of a phospholipid (with 55% phosphatidylcholine-containing lecithin as an example) was added, and emulsification and dissolution were conducted; 300 kg of NR was added, and then 2 kg of calcium chloride was added; a resulting mixture was stirred and heated to 45° C. to 50° C. until the mixture was uniformly emulsified, and a pH was adjusted to 5.8 to 6.3 with a hydrochloric acid or sodium hydroxide solution; and PLD and PLC were added simultaneously to allow a reaction for about 4 h to obtain 121 kg of β-NMN.

Example 25

Preparation of β-NMN Through One-Pot Synthesis in Which Enzymes Were Added Successively 1,000 L of drinking water was added to a reactor, then 20 kg of a phospholipid (with 60% phosphatidylcholine-containing lecithin as an example) was added, and emulsification and dissolution were conducted; 36 kg of NR was added, and then 0.1 kg of calcium chloride was added; a resulting mixture was stirred and heated to 45° C. to 50° C. until the mixture was uniformly emulsified, and a pH was adjusted to 5.8 to 6.3 with a hydrochloric acid or sodium hydroxide solution; and PLD and PLC were added simultaneously to allow a reaction for about 2 h to obtain 4.1 kg of β-NMN.

Example 26

Preparation of β-NMN Through One-Pot Synthesis in Which Enzymes Were Added Successively 5,000 L of a mixture of water, n-heptane, and isopropanol in a ratio of 7.5:2:0.5 was added to a reactor, then 800 kg of a phospholipid (with 70% phosphatidylcholine-containing lecithin as an example) was added, and emulsification and dissolution were conducted; 250 kg of NR was added, and then 100 kg of calcium chloride was added; a resulting mixture was stirred and heated to 45° C. to 50° C. until the mixture was uniformly emulsified, and a pH was adjusted to 5.8 to 6.3 with a hydrochloric acid or sodium hydroxide solution; and PLD and PLC were added simultaneously to allow a reaction for about 6 h to obtain 222 kg of β-NMN.

Example 27

Preparation of β-NMN Through One-Pot Synthesis in Which Enzymes Were Added Simultaneously 3,000 L of a mixture of water and isopropanol in a ratio of 7:3 was added to a reactor, then 600 g of a phospholipid (with 50% phosphatidylcholine-containing lecithin as an example) was added, and emulsification and dissolution were conducted; 100 kg of NR was added, and then 2 kg of calcium chloride was added; a resulting mixture was stirred and heated to 45° C. to 50° C. until the mixture was uniformly emulsified, and a pH was adjusted to 5.8 to 6.3 with a hydrochloric acid or sodium hydroxide solution; and PLD and PLC were added simultaneously to allow a reaction for about 5 h to obtain 105 kg of β-NMN.

Example 28

Preparation of β-NMN Through One-Pot Synthesis in Which Enzymes Were Added Simultaneously 3,000 L of water was added to a reactor, then 600 g of a phospholipid (with 50% phosphatidylcholine-containing lecithin as an example) was added, and emulsification and dissolution were conducted; 45 kg of NR was added, and then 1 kg of calcium chloride was added; a pH was adjusted to 5.8 to 6.3 with a hydrochloric acid or sodium hydroxide solution; and PLD and PLC were added simultaneously to allow a reaction for about 2 h to obtain 26 kg of β-NMN.

What is claimed is:

1. A synthesis method of β-nicotinamide mononucleotide (β-NMN), wherein the synthesis method is conducted by a method selected from the group consisting of (a) and (b):

(a): two-step enzymolysis, comprising:

a1: contacting nicotinamide riboside (NR) and a phospholipid with a phospholipase D (PLD) in the presence of a calcium ion to conduct a catalytic reaction to produce phosphatidyl nicotinamide riboside (PNR); and a2: contacting the PNR produced in step a1 with a phospholipase C (PLC) in the presence of a calcium ion to conduct a catalytic reaction to produce the β-NMN;

(b): one-pot synthesis to prepare the β-NMN, wherein the one-pot synthesis to prepare the β-NMN is conducted by a one-pot synthesis method selected from the group consisting of (1) and (2):

(1): combining NR, a phospholipid, and a calcium ion, and adding a PLD to allow a first catalytic reaction to produce PNR, and after the first reaction is completed, adding a PLC to allow a second reaction to obtain the β-NMN;

(2): combining NR, a phospholipid, and a calcium ion, and adding a PLD and a PLC together to allow a catalytic reaction to obtain the β-NMN.

2. The synthesis method according to claim 1, wherein the PNR is I:

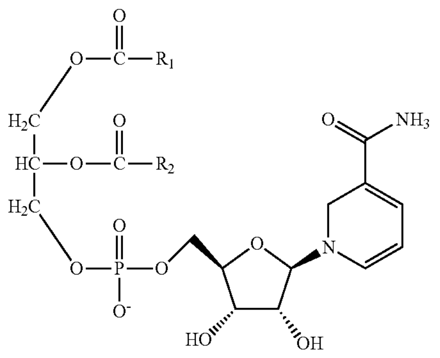

wherein $R_1$ and $R_2$ each are fatty acyl; and wherein $R_1$ and $R_2$ are natural phospholipids that are $C_{14-24}$ fatty acids.

3. The synthesis method according to claim 1, wherein:

a molar ratio of the NR to the phospholipid in a1 is 1:10 to 10:1;

a concentration of the calcium ion is 0.01 g/L to 20 g/L; and the catalytic reaction of the PLD is conducted at a temperature of 20° C. to 70° C. and a pH of 4.5 to 7.5.

4. The synthesis method according to claim 1, wherein during the catalytic reaction of the PLD, an additive is further added, and the additive comprises, but is not limited to, one or more selected from the group consisting of n-hexane, n-heptane, and isopropanol.

5. The synthesis method according to claim 1, wherein in a2, a concentration of the calcium ion in a reaction system is 0.01 g/L to 20 g/L; and the catalytic reaction of the PLC is conducted at a temperature of 20° C. to 70° C. and a pH of 4.0 to 7.0.

6. The synthesis method according to claim 5, wherein during the catalytic reaction of the PLC, an alkane and/or a short-chain alcohol are/is further added as an additive; wherein the alkane is one or two selected from the group consisting of n-hexane and n-heptane; and wherein the short-chain alcohol is one or two selected from the group consisting of methanol, ethanol, propanol, isopropanol, butanol, and pentanol.

7. The synthesis method according to claim 2, wherein the natural phospholipids $R_1$ and $R_2$ are selected from the group consisting of $C_{16}$ and $C_{18}$ fatty acids.

8. The synthesis method according to claim 2, wherein $R_1$ is selected from the group consisting of $-C_{15}H_{31}$, $-C_{17}H_{35}$, and $-C_{17}H_{33}$; and wherein $R_2$ is selected from the group consisting of $-C_{17}H_{31}$, $-C_{19}H_{29}$, $-C_{19}H_{31}$, $-C_{21}H_{31}$, and $-C_{17}H_{33}$.

9. The synthesis method according to claim 1, wherein the phospholipid comprises phosphatidylcholine and/or phosphatidylethanolamine.

10. The synthesis method according to claim 9, wherein the phospholipid is lecithin.

11. The synthesis method according to claim 1, wherein the PLC is a broad-spectrum PLC.

12. The synthesis method according to claim 11, wherein the PLC is a phosphatidylinositol-specific phospholipase C (PIPLC).

13. The synthesis method according to claim 1, wherein the PLD is a PLD derived from a microorganism.

14. The synthesis method according to claim 3, wherein the molar ration of the NR to the phospholipid in a1 is 1:5 to 5:1;

the concentration of the calcium ion is 0.5 g/L to 5 g/L; and the catalytic reaction of the PLD is conducted at a temperature of 40° C. to 60° C. and a pH of 5.0 to 6.5.

15. The synthesis method according to claim 14, wherein the molar ration of the NR to the phospholipid in a1 is 1:2 to 3:1.

16. The synthesis method according to claim 5, wherein in a2, the concentration of the calcium ion is 0.1 g/L to 2 g/L; and the catalytic reaction of the PLC is conducted at a temperature of 40° C. to 55° C. and a pH of 5.0 to 7.0.

* * * * *